United States Patent
Pradel

(10) Patent No.: US 7,469,589 B2
(45) Date of Patent: Dec. 30, 2008

(54) METHOD AND DEVICE FOR DETERMINING THE LIMPNESS OF SHEET MATERIAL BY MEANS OF ULTRA-SOUND

(75) Inventor: Helmut Pradel, München (DE)

(73) Assignee: Giesecke & Devrient GmbH, Munich (DE)

( * ) Notice: Subject to any disclaimer, the term of this patent is extended or adjusted under 35 U.S.C. 154(b) by 134 days.

(21) Appl. No.: 10/554,217

(22) PCT Filed: Apr. 20, 2004

(86) PCT No.: PCT/EP2004/004176

§ 371 (c)(1),
(2), (4) Date: Sep. 22, 2006

(87) PCT Pub. No.: WO2004/095380

PCT Pub. Date: Nov. 4, 2004

(65) Prior Publication Data

US 2007/0006654 A1    Jan. 11, 2007

(30) Foreign Application Priority Data

Apr. 22, 2003  (DE) ................................ 103 18 104

(51) Int. Cl.
   *G01N 29/04*   (2006.01)
(52) U.S. Cl. .............................. 73/602; 73/597; 73/628
(58) Field of Classification Search .................... 73/602, 73/597, 598, 599, 600, 620, 624, 625, 627, 73/628, 629, 159; 209/534, 590, 576, 577, 209/587, 588, 599
See application file for complete search history.

(56) References Cited

U.S. PATENT DOCUMENTS

| 4,519,249 | A | * | 5/1985 | Hunt | 73/596 |
|---|---|---|---|---|---|
| 4,612,807 | A | | 9/1986 | Wunderer | |
| 4,976,150 | A | * | 12/1990 | Deka | 73/644 |
| 5,672,828 | A | * | 9/1997 | Allan | 73/579 |
| 5,922,959 | A | | 7/1999 | Kayani | |
| 5,938,334 | A | * | 8/1999 | Kayani | 374/44 |
| 6,026,681 | A | | 2/2000 | Wunderer et al. | |
| 6,115,127 | A | | 9/2000 | Brodeur et al. | |
| 6,407,964 | B1 | * | 6/2002 | Hornung et al. | 367/138 |
| 6,424,597 | B1 | * | 7/2002 | Bolomey et al. | 367/138 |
| 6,595,060 | B2 | * | 7/2003 | Wunderer et al. | 73/597 |
| 6,745,628 | B2 | | 6/2004 | Wunderer | |

(Continued)

FOREIGN PATENT DOCUMENTS

DE        3 424 652        1/1986

(Continued)

*Primary Examiner*—Hezron E. Williams
*Assistant Examiner*—Jacques M. Saint-Surin
(74) *Attorney, Agent, or Firm*—Bacon & Thomas, PLLC

(57) ABSTRACT

The invention relates to an apparatus used in a method for determining the limpness of sheet material, in particular of bank notes, wherein the sheet material is irradiated with sound waves, sound waves emanating from the sheet material are captured and the limpness of the sheet material is determined therefrom. An especially simple and reliable determination of limpness even independent of the degree of soiling of the sheet material can be achieved by measuring both the transmitted and the reflected sound waves and to form a mathematical ratio of the reflected and transmitted soundwaves, in order to determine the limpness.

17 Claims, 1 Drawing Sheet

U.S. PATENT DOCUMENTS

2003/0025512 A1 2/2003 Wunderer
2007/0187209 A1* 8/2007 Stenzel et al. ............... 194/206

FOREIGN PATENT DOCUMENTS

| | | |
|---|---|---|
| DE | 100 29 442 | 1/2002 |
| DE | 101 37 389 | 2/2003 |
| EP | 0 449 642 | 10/1991 |
| EP | 0 470 808 | 2/1992 |

* cited by examiner

METHOD AND DEVICE FOR DETERMINING THE LIMPNESS OF SHEET MATERIAL BY MEANS OF ULTRA-SOUND

BACKGROUND OF THE INVENTION

1. Field

The invention relates to a method and an apparatus for determining the limpness of sheet material, in particular of bank notes, wherein the sheet material is irradiated with sound waves, the sound waves emanating from the irradiated sheet material are measured, and the determination of the limpness of the sheet material is effected on the basis of the measured sound waves.

2. Related Art

Such a system is known for example from the U.S. Pat. No. 5,922,959. Here the sound portion reflected by a bank note exposed to sound waves is measured. The lesser sound reflected by the checked bank note, the greater the degree of limpness of the bank note. Furthermore, there is described that alternatively also the degree of sound wave transmission can be determined.

This known proceeding, however, has the disadvantage that the degree of limpness of the bank notes can be determined in an only insufficient manner. Other influence quantities, such as the degree of soiling of the bank note, folds or crumple, also lead to a changed absorption of sound, so that the information about the limpness of the bank note paper required in the known system cannot be obtained in a clear fashion by means of the known method.

On these premises, it is the problem of the present invention to provide a method and an apparatus for determining the limpness of sheet material, that have a higher accuracy.

BRIEF SUMMARY OF THE INVENTION

This problem is solved by the method according to claim 1 and the apparatus according to claim 10. The further claims describe preferred embodiments.

An essential idea of the present invention is based on the fact, that both the sound reflected by the sheet material and the transmitted sound are measured and a mathematical ratio of the reflected and the transmitted sound waves is formed in order to determine the limpness. Such a ratio formation for example can be the formation of a difference or of a quotient of the intensities of the measured signals. By taking into consideration these two sound portions when measuring it is possible to reduce the influences other properties of the sheet material may have, such as e.g. its state, degree of soiling, weight per unit area etc. These measurings especially preferred are taken from a common place of the sheet material, since when measuring at different places, e.g. due to differing degrees of soiling, inaccuracies can occur when determining the limpness. Moreover, the irradiation and evaluation may be effected not only locally, but additionally or alternatively also over the whole area.

Beside the above-mentioned variant of forming a ratio of transmitted and reflected sound wave, there are further proceedings, which likewise may be employed independently of each other and of the above-mentioned solution according to the invention.

For compensating the mentioned sheet material properties, there can also be provided, for example, that beside measuring the limpness a further measuring for determining this sheet material property, such as the nominal value, the weight per unit area, or the degree of soiling of the irradiated place of the sheet material, is carried out, and this sheet material property is taken into consideration when determining the limpness. This means e.g. that before measuring the limpness or alternatively also following such a measuring a separate measuring of the soiling is effected, and the measure obtained for the degree of soiling can be taken into consideration when forming a reference value, with which the results of the acoustic limpness measuring are compared, so as to decide on the degree of limpness. The measuring of the degree of soiling can be effected with the help of the known methods, e.g. according to DE 27 52 412 A1, DE 29 32 962 A1 or DE 100 05 514 A1.

The accuracy of the limpness evaluation preferably can also be increased by taking into consideration the nominal value of the respective bank note that is already known or determined by measuring before. This can be effected e.g. by selecting different reference values for different nominal values.

A further independent idea of the present invention is, that not only the intensity and therewith the portion of reflected or transmitted sound waves is measured, but the frequency spectrum of the measured sound waves is determined. Limp bank notes e.g. have a frequency spectrum different from that of not limp bank notes. Here a measuring of at least one frequency band and/or a plurality of discrete frequencies can be effected. Moreover, an evaluation of the intensity and/or phase of the different frequencies can be carried out. In particular with this measuring preferably a pulse excitation and/or an excitation with a plurality of frequencies is effected.

A further independent idea of the present invention is to measure the transit time of sound waves within the sheet material. For example, a bank note can be irradiated with a certain acoustic pulse at a certain place of the paper at a certain point of time, and e.g. with the aid of an optical interferometer the following deflection of the bank note can be measured at a place spaced apart from the mentioned place in a time-resolved fashion, so as to obtain a measure for the propagation of the sound wave in the bank note paper. The transit time and/or the dimension of the deflection usually depends on the degree of limpness of the bank note. The transit time preferably can be measured at a plurality of frequencies and the measuring can be evaluated at a plurality of frequencies.

A further independent idea of the present invention is to carry out the excitation of the sheet material and/or the measuring of the sound waves emanating from the sheet material in a contacting fashion. Preferably, an ultrasonic transducer for emitting and/or receiving sound waves can be disposed such that it partially or completely is in contact or comes in contact with a sheet to be checked. By this means, compared to a contactless excitation/measuring, the efficiency is increased and disturbing effects caused by the transmission through air are reduced.

DESCRIPTION OF THE DRAWING

In the following the present invention is described in more detail with reference to the accompanying Figures.

DETAILED DESCRIPTION OF THE PREFERRED EMBODIMENTS OF THE INVENTION

Figure 1:
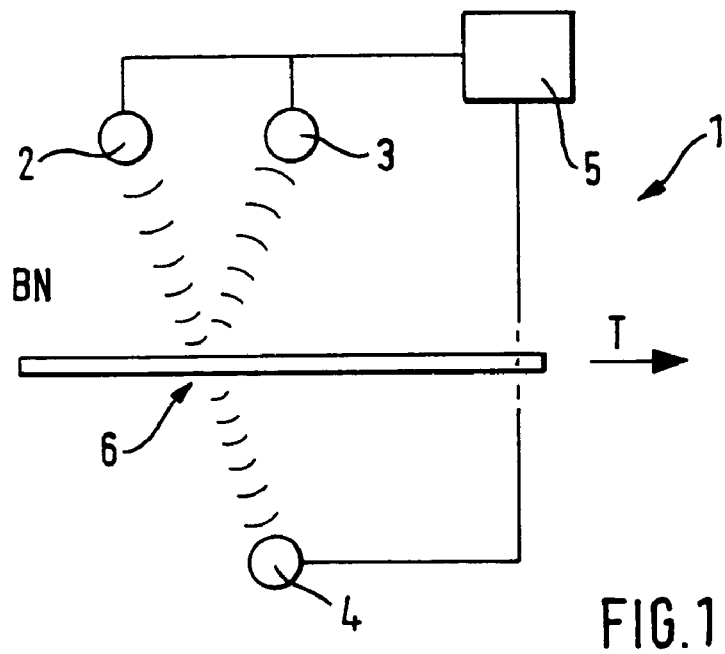
FIG. 1 shows a schematic side view of a checking apparatus for determining the limpness according to a first embodiment.

FIG. 1 shows a first example for a checking apparatus 1 for determining the limpness of bank notes BN. The checking apparatus 1 can be integrated in the way known in the art in an apparatus for processing bank notes BN, in which singled bank notes are transported past the checking device 1 in the direction of T. The apparatus 1 here in particular has a source of sound 2 for irradiating the sheet material with sound waves and a measuring device for measuring the sound waves reflected and transmitted by the irradiated sheet material. In particular, the measuring device has a reflection sensor 3 for measuring the sound portion reflected by the bank note BN and a transmission sensor 4 for measuring the sound portion transmitted through the bank note BN.

Moreover, the apparatus 1 has an evaluation unit 5, which via signal lines is connected with the source of sound 2 and the sensors 3, 4 and is adapted to evaluate the signals of these components, in order to determine the limpness of the checked bank note BN. Though not restricted to this, the source of sound 2 preferably emits ultrasonic waves. The frequencies lie e.g. within a range of 100 to 400 kilohertz. The source of sound 2 and the sensors 3, 4 are disposed in such a way and have such a radiation characteristic or measuring characteristic, that they can measure the sound portions emanating from the same place 6. Then in the evaluation unit 5 the sound portions measured for a place 6 are compared to each other and are related to each other e.g. by way of a difference ratio or a quotient ratio of the sound intensities, which is compared with one or a plurality of predetermined reference values, in order to determine the degree of limpness. This measure for the limpness of the bank note BN may partially compensate influence quantities such as the weight per unit area or the degree of soiling of the bank note BN, which otherwise would have a disturbing effect on the measuring. The place 6, which is exposed to sound waves and where the measuring is effected, may extend only over a partial area of the bank note surface. However, it is also possible, that the bank note is irradiated over a large surface and the measuring likewise is effected over a large surface and/or the measured values of a plurality of places 6 of one single bank note BN are collected and e.g. the evaluation is effected with an average value. Moreover, it is thinkable, that the bank note BN prior to the evaluation of the limpness measuring is checked as to defects, such as e.g. tears, holes or the like, and the evaluation of the limpness measuring is not carried out at such defect places.

Figure 2:
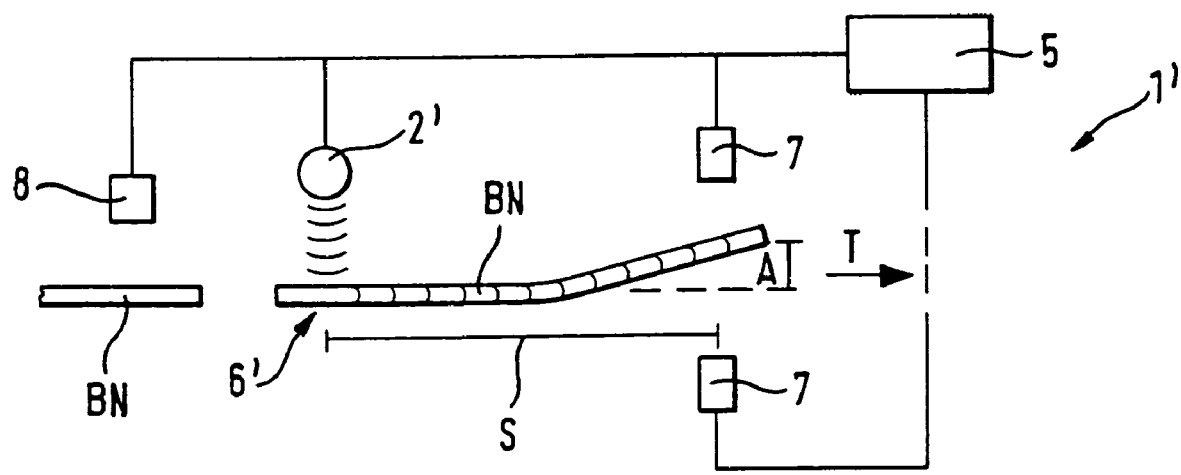
FIG. 2 shows a schematic side view of an apparatus for determining the limpness according to a second embodiment.

The FIG. 2 shows a second embodiment of the present invention. The apparatus 1' again comprises a source of sound 2' for the acoustic irradiation of a bank note BN to be checked and likewise comprises the not shown sensors 3 and 4 for capturing reflected or transmitted sound.

However, this variant is especially characterized in that it additionally or alternatively serves for measuring the transit time of the sound waves in the bank note. For this purpose the apparatus 1' preferably has two optical sensors 7 located on mutually opposite sides. This sensors 7 can be e.g. optical interferometers 7, which are adapted to determine a deflection A of the bank note BN caused by an acoustic excitation. In particular, a bank note BN to be checked at a certain place 6' and at a given time is locally exposed to a short acoustic pulse emitted by the source of sound 2', and thereafter in a time-resolved fashion the optical interferometers 7 determine the deflection A of the bank note BN in the area between the two mutually opposing interferometers 7, this area being at a distance to the place 6'. The measured signals are evaluated in the evaluation unit 5 to the effect as to determine the length of the transit time of the sound for the path S between the point of sound exposure 6' and the measuring area of the two interferometers 7. The measure for the transit time is used alone or in combination with the measurings of the reflected or transmitted sound portions for determining the limpness. It is assumed, that the transit time in the bank note paper is the longer, the greater the degree of limpness and thus the damage of the inner structure of the bank note paper. Alternatively, the determination of the transit time of the sound by capturing the deflection A of the bank notes BN at spaced apart places can be determined also with other measuring methods than optical interferometry.

As a further feature the checking device 1' according to FIG. 2 optionally has a sensor for measuring other bank note properties, such as e.g. a soiling sensor 8, which e.g. can be designed according to DE 29 32 962 A1, in order to determine the degree of soiling of a bank note BN. The soiling sensor 8 e.g. can be adapted to receive light in the invisible spectral region, so as to therefrom determine the degree the soiling of the bank note BN. The soiling sensor 8 preferably is located upstream of the limpness sensor when transporting the individual bank notes BN in the direction of T. The determination of the degree of soiling with the soiling sensor 8 preferably is effected at the same place, at which in the following the limpness is determined. Since a soiled bank note BN usually should absorb more sound than a not soiled bank note BN, independently of the degree of limpness, the results determined by means of the soiling sensor 8 regarding the degree of soiling of a bank note BN to be checked can be taken into consideration with the subsequent evaluation in the evaluation unit 5 for determining the limpness. Additionally or alternatively, instead of the soiling also the nominal value or the weight per unit area of the bank note BN can be precedingly determined and taken into consideration when evaluating the limpness.

This variant with an upstream sensor for measuring other bank note properties, such as the soiling sensor 8, in particular is of advantage for other acoustic limpness measurings, wherein e.g. not the ratio of transmitted and reflected sound intensity, but merely the reflected or alternatively the transmitted sound portion is determined in an already known fashion. In this case e.g. at least the one reference value, to which the measured sound intensity is compared for the purpose of determining the limpness, is selected differently in dependence on the measured degree of soiling.

Beside the above-mentioned variations further designs are thinkable. The sensors 3, 4, which serve for measuring reflected or transmitted sound waves, preferably can be designed as broadband microphones, which are able to capture a wide frequency spectrum of the measured sound signals, so that the said frequency spectrum can be evaluated in the evaluation unit 5. The sound sensors 3, 4 preferably can have broadband microphones with a recording characteristic within the range of 0.1 kilohertz to 200 kilohertz.

In particular, in this case a broadband excitation by means of acoustic irradiation with an acoustic pulse or a mechanical excitation by deflecting or diverting the bank note is effected. For example the BN can be deflected along a runner in the transport path and the resulting noises are measured in a broadband fashion.

The frequency spectrum of the sound waves that emanate from the bank note BN to be checked has characteristic forms for limp bank notes that are different to that of not limp bank notes. It shall be emphasized, that this idea of evaluating the frequency spectrum and not only the intensity of the measured sound waves can also be used independently of the acoustic excitation. For example, it is also usable with an already known mechanical excitation of bank notes and subsequent measuring of the sound waves emanating from the mechanically excited bank note.

Preferably, the sources of sound and/or the measuring devices are in contact with the sheet material to be measured, so as to achieve an improved signal transmission with less disturbing effects.

Consequently, the present invention in its different variations permits a simple and reliable determination of the limpness of bank notes.

The invention claimed is:

1. A method for determining the limpness of sheet material, comprising the steps:
   irradiating the sheet material with sound waves,
   measuring the sound waves reflected by the sheet material and transmitted by the sheet material, and,
   determining the limpness of the sheet material on the basis of the measured sound waves, wherein the step of determining the limpness of the sheet material comprises forming a mathematical ratio of the reflected and the transmitted sound waves to determine the limpness.

2. The method according to claim 1, wherein the measuring of the reflected and the transmitted sound waves is taken from a common place on the sheet material.

3. The method according to claim 1, wherein a measure for a property of the sheet material other than the limpness-is determined and is taken into consideration when determining limpness.

4. The method according to claim 1, wherein a measure of the sound waves irradiating the sheet material is obtained and taken into consideration when forming the ratio for determining the limpness.

5. The method according to claim 1, wherein the frequency spectrum of the sound waves is measured and taken into consideration when determining the limpness.

6. The method according to claim 1, wherein the transit time of sound waves in the sheet material is measured and taken into consideration when determining the limpness.

7. The method according to claim 6, wherein for determining the transit time of sound waves in the sheet material, a measurement of the deflection of the sheet material is carried out.

8. The method according to claim 1, wherein defective areas of the sheet material are determined and these areas are not taken into consideration when determining the limpness.

9. The method according to claim 1, wherein at least one of the steps of excitation of the sheet material and the measuring of the sound waves emanating from the sheet material is carried out in a contacting fashion.

10. The method according to claim 1, wherein the property of the sheet material other than the limpness that is determined as selected from the group consisting of the nominal value of the sheet material; the weight per unit area of the sheet material; and the degree of soiling of the sheet material.

11. An apparatus for determining the limpness of sheet material comprising:
   a source of sound for irradiating the sheet material with sound waves,
   a measuring device for measuring the sound waves which emanate from the irradiated sheet material, the measuring device comprising both a reflection sensor for measuring the sound waves reflected by the sheet material and a transmission sensor for measuring the sound waves transmitted through the sheet material;
   an evaluation unit for determining the limpness of the sheet material on the basis of the sound waves captured by the measuring device, the evaluation unit being arranged to form a mathematical ratio of the reflected and transmitted sound waves measured and to use said mathematical ratio to determine the limpness.

12. The apparatus according to claim 11, wherein the evaluation unit is arranged to form a mathematical ratio of the reflected and the transmitted sound waves emanating from a common place on the sheet material.

13. The apparatus according to claim 11, wherein the measuring device comprises a broadband microphone in order to determine the frequency spectrum of the captured sound waves.

14. The apparatus according to claim 11, wherein said measuring device comprises a unit for determining the transit time of sound waves in the sheet material.

15. The apparatus according to claim 11, wherein said measuring device comprises a unit for determining a property of the sheet material other than the limpness.

16. The apparatus according to claim 15, wherein said unit for determining a property of the sheet material other than the limpness is selected from the group consisting of the nominal value of the sheet material; the weight per unit area of the sheet material; and the degree of soiling of the sheet material.

17. The apparatus according to claim 11, wherein at least one of the source of sound and the measuring device is in contact with the sheet material to be measured.

* * * * *